US008722328B2

(12) United States Patent
Khripin et al.

(10) Patent No.: US 8,722,328 B2
(45) Date of Patent: May 13, 2014

(54) METHODS, COMPOSITIONS, AND KITS FOR RECOVERY OF NUCLEIC ACIDS OR PROTEINS FROM FIXED TISSUE SAMPLES

(75) Inventors: Yuri Khripin, Gaithersburg, MD (US); Arvind Virmani, Gaithersburg, MD (US); Lori Kobayashi, Boonsboro, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 263 days.

(21) Appl. No.: 12/984,391

(22) Filed: Jan. 4, 2011

(65) Prior Publication Data

US 2011/0196146 A1    Aug. 11, 2011

Related U.S. Application Data

(60) Provisional application No. 61/292,078, filed on Jan. 4, 2010.

(51) Int. Cl.
*C12Q 1/68* (2006.01)
*B01L 3/00* (2006.01)
*C12P 19/34* (2006.01)

(52) U.S. Cl.
USPC .......................... 435/6.1; 435/91.1; 422/430

(58) Field of Classification Search
USPC .................... 435/6.1, 91.1; 422/430
See application file for complete search history.

(56) References Cited

U.S. PATENT DOCUMENTS

| | | | |
|---|---|---|---|
| 4,894,325 | A | 1/1990 | Englehardt et al. |
| 7,439,016 | B1 | 10/2008 | Anthony et al. |
| 7,812,144 | B2 | 10/2010 | Karlsen |
| 2003/0175789 | A1 | 9/2003 | Weininger et al. |
| 2005/0032038 | A1 | 2/2005 | Fisher et al. |
| 2005/0032105 | A1 | 2/2005 | Bair et al. |
| 2006/0051809 | A1 | 3/2006 | Nazarenko |
| 2006/0240449 | A1 | 10/2006 | McGlennen et al. |
| 2007/0154884 | A1 | 7/2007 | Lorincz |
| 2009/0286687 | A1 | 11/2009 | Dressman et al. |
| 2010/0311039 | A1 | 12/2010 | Lowe et al. |

FOREIGN PATENT DOCUMENTS

| | | |
|---|---|---|
| EP | 0287961 A2 | 10/1988 |
| EP | 0333465 | 9/1989 |
| EP | 0540170 A1 | 5/1993 |
| EP | 1 806 410 A2 | 7/2007 |
| EP | 2 184 368 A1 | 5/2010 |
| JP | 2009 106220 | 5/2009 |
| WO | 8607387 | 12/1986 |
| WO | 99/02488 | 1/1999 |
| WO | 01/96608 | 12/2001 |
| WO | 2004/087950 | 10/2004 |
| WO | 2007/056723 | 5/2007 |
| WO | 2007/130519 A2 | 11/2007 |
| WO | 2008/036061 | 3/2008 |
| WO | 2008/139938 A1 | 11/2008 |
| WO | 2009/057993 A1 | 5/2009 |
| WO | 2009/123996 | 10/2009 |
| WO | 2010/004251 A1 | 1/2010 |
| WO | 2010/028382 | 3/2010 |
| WO | 2010/127228 A1 | 11/2010 |

OTHER PUBLICATIONS

Kazachkov et al., "Evidence for in Vivo Scavenging by Aminoguanidine of Formaldehyde Produced via Semicarbazide-Sensitive Amine Oxidase-Mediated Deamination," The Journal of Pharmacology and Experimental Therapeutics, 2007, pp. 1201-1207, vol. 322, No. 3.
Goldstein, A., "Dihydrazides—The Versatile Curing Agent for Solid Dispersion Systems," A&C Catalysts, Inc., Apr. 2000 (www.ac-catalysts.com).
"Chemistry of Crosslinking," Thermo Fisher Scientific, Inc., 2010, pp. 1-8 (piercenet.com/browse.cfm?fldID=CE4D6C5C-5946-4814-9904-C46E01232683).
Lowe et al.; "A Hybrid-Capture Assay to Detect HPA MRNA Ratios in Cervical Specimens"; Journal of Virological Methods; vol. 179; No. 1; Jan. 2012; pp. 142-147.
International Search Report Based on Application No. PCT/US2012/026380 Mailed Oct. 15, 2012.
International Search Report and Written Opinion of PCT/US2010/048714, dated Dec. 10, 2010 (14 pages).
International Preliminary Report on Patentability and Written Opinion of PCT/US2009/041033, dated Oct. 19, 2010 (6 pages).
International Search Report and Written Opinion of PCT/US2010/047769, dated Nov. 9, 2010 (11 pages).
Pachowics, et al., "Sequence specific large volume sample prep solution utilizing Hybrid Capture technology," 41st Annual Oak Ridge Conference; Baltimore, MD; Apr. 16, 2009; retrieved from the Internet: http://www.aacc.org/events/meeting_proceeding/2009/Documents/OakRidge09AllPosters.pdf.
Keegan et al., "Comparison of HPV detection technologies: Hybrid capture 2, PreTect HPV-Proofer and analysis of HPV DNA viral load in HPV16, HPV18 and HPV33 E6/E7 mRNA positive specimens," Journal of Virological Methods, Jan. 1, 2009, pp. 61-66, vol. 155, No. 1, Elsevier BV, XP025799776.
Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.
Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.
Nazarenko et al., "A novel method of HPV genotyping using Hybrid Capture sample preparation method combined with GP5+/6+ PCR and multiplex detection on Luminex XMAP," Journal of Virological Methods, Dec. 1, 2008, pp. 76-81, vol. 154, No. 1-2, Elsevier BV, XP025680302.

(Continued)

*Primary Examiner* — Jezia Riley
(74) *Attorney, Agent, or Firm* — Miles & Stockbridge, PC

(57) ABSTRACT

Methods and materials for improving nucleic acid or protein recovery from samples preserved in liquid cytological preservative solutions by utilizing scavenging agents, such as hydrazine- and hydrazide-containing compounds, are provided. Lysis solutions comprising hydrazine- and hydrazide-containing compounds and kits comprising the same are also provided.

26 Claims, 9 Drawing Sheets

(56) References Cited

OTHER PUBLICATIONS

Taha et al., "Universal Collection Medium (UCM) is as suitable as the Standard Transport Medium (STM) for Hybrid Capture II (HC-2) assay," Journal of Virological Methods, May 1, 2006, pp. 32-35, vol. 36, No. 1, Elsevier BV, XP025178639.

Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol. 16, No. 3, Lippincott-Raven Publishers, XP008011933.

Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Science, XP002603500.

Tsai et al., "Association between Quantitative High-Risk Human Papillomavirus DNA Load and Cervical Intraepithelial Neoplasm Risk," Cancer Epidemiology, Biomarkers & Prevention: American Association for Cancer Research, Nov. 2005, pp. 2544-2549, vol. 14, No. 11 pt 1, XP002603501.

Moodley et al., "Human papillomavirus prevalence, viral load and pre-cancerous lesions of the cervix in women initiating highly active antiretroviral therapy in South Africa: a cross-sectional study," BMC Cancer, Aug. 7, 2009, pp. 1-8, vol. 9, No. 275, Biomed Central Ltd, XP002603502.

Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.

International Search Report Based on Application No. PCT/US2012/020684 Mailed Oct. 25, 2012.

Clad et al.; "Performance of the Aptima High-Risk Human Papillomavirus MRNA Assay in a Referral Population in Comparison With Hybrid Capture 2 and Cytology"; Journal of Clinical Microbiology; Mar. 2011; LNKD-Pubmed:21191046; vol. 49; No. 3; Dec. 29, 2010; pp. 1071-1076; Abstract.

Li et al; Detection of Human Papillomavirus Genotypes With Liquid Bead Microarray in Cervical Lesions of Northern Chinese Patients; Cancer Genetics and Cytogenetics, Elsevier Science Publishing, New York, NY, US; vol. 182; No. 1; Mar. 6, 2008; pp. 12-17; Abstract.

Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US ; vol. 44; No. 6; Jun. 1, 2006; pp. 2025-2031; Abstract.

Han et al.; "Simultaneous Amplification and Identification of 25 Human Papillomavirus Types With Templex Technology"; Journal of Clinical Microbiology 200611 US Lnkd-DOI:10.1128/JCM.01762-06; vol. 44; No. 11; Nov. 2006; pp. 4157-4162; Abstract.

Database Embl [Online]; Jul. 19, 2007; "Sequence 25 From Patent EP1806410"; XP002675256; Retrieved From EBI Accession No. Embl:CS642417; Database Accession No. CS642417.

Database Embl [Online]; Dec. 14, 2010; "Sequence 26 From Patent US 7812144"; XP00267527; Retrieved From EBI Accession No. Embl:GX640151; Database Accession No. GX640151.

Database Geneseq [Online]; Jan. 22, 2009; "HPV-16 E7/E6 Gene Target Sequence, Bases 752-774"; XP002675258, Retrieved From EBI Accesssion No. GSN:ATS82292; Database Accession No. ATS82292.

Database Geneseq [Online]; Jan. 22, 2009; "HPV-16 E7/E6 Gene Target Sequence, Bases 698-720"; XP002675259 Retrieved From EBI Accession No. GSN:ATS82290; Database Accession No. ATS82290; The Whole Document.

Database Geneseq [Online]; Apr. 1, 2010; "HPV16 E7 Gene Forward RT-PCR Primer Seq ID 49"; XP002675260; Retrieved From EBI Accession No. GSN:AXU96631; Database Accession No. AXU96631; The Whole Document.

Database Geneseq [Online]; Apr. 21, 2005; "E7 Coding Region (1-87) Amplifying Sense PCR Primer, Seq ID No. 37"; XP002675261; Retrieved From EBI Accession No. GSN:ADX15568; Database Accession No. ADX15568; Sequence.

International Search Report and Written Opinion of PCT/US2011/22887, dated Jun. 1, 2011.

International Preliminary Report on Patentability and Written Opinion of PCT/US2009/062061, dated May 12, 2011.

International Preliminary Report on Patentability and Written Opinion of PCT/US2009/062041, dated May 12, 2011.

GenBank Submission FJ429103. 2009 [Retrieved from the Internet May 20, 2011: <www.ncbi.nlm.nih.gov/nuccore/FJ429103.1>]; in entirety.

Yevgeniy S Belousov et al.: "Single nucleotide polymorphism genotyping by two colour melting curve analysis using the MGB elicpse TM probe system in challenging sequence environment" Human Genomics, Henry Stewart Publications, London, GB, vol. 1, No. 3, Jan. 1, 2004, pp. 209-217; XP001538494.

International Search Report and Written Opinion based on PCT/US2011/037012 mailed Apr. 17, 2012.

Chinese First Action dated Apr. 26, 2013, issued in Application No. 201180012414.0 and English translation thereof.

Gilbert et al., "The Isolation of Nucleic Acids from Fixed, Paraffin-Embedded Tissues-Which Methods are Useful When?", PLOS One, Jun. 6, 2007, vol. 2, No. 6, pp. 1-12.

Rivero et al., "Simple Salting-Out Method for DNA Extraction from Formalin-Fixed, paraffin-Embedded Tissues", Pathology Research and Practice, Jul. 10, 2006, vol. 202, No. 7, pp. 523-529.

International Search Report and Written Opinion of PCT/US2011/020107, dated Jul. 12, 2011.

Lowe et al., "HPV Genotype Detection Using Hybrid Capture Sample Preparation Combined with Whole Genome Amplification and Multiplex Detection with Luminex XMAP," Journal of Molecular Diagnostics; Nov. 6, 2010; pp. 847-853; vol. 12; No. 6; American Society for Investigative Pathology.

Partial European Search Report of EP10185824; mailed Feb. 16, 2011 (8 pages).

Scott et al., "Detection of herpes simplex virus type 1 shedding in the oral cavity by polymerase chain reaction and enzyme-linked immunosorbent assay at the prodromal stage of recrudescent herpes labialis," Journal of Oral Pathology & Medicine; Aug. 1997; pp. 305-309; vol. 26; No. 7; XP009143938.

Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.

METHODS, COMPOSITIONS, AND KITS FOR RECOVERY OF NUCLEIC ACIDS OR PROTEINS FROM FIXED TISSUE SAMPLES

REFERENCE TO RELATED APPLICATIONS

This application claims priority to U.S. Provisional Patent Application No. 61/292,078, filed on Jan. 4, 2010, which is incorporated herein by reference in its entirety.

FIELD OF THE INVENTION

Methods and kits for improving recovery of nucleic acids or proteins that have been fixed in tissue or cell samples are described.

BACKGROUND OF THE INVENTION

In the fields of histology, pathology, and cell biology, fixation is a chemical process by which biological samples are preserved from decay. Fixation terminates any ongoing biochemical reactions, and may also increase the mechanical strength or stability of the treated samples. The purpose of fixation is to preserve a sample of biological material as close to its natural state as possible. Fixed samples are used for examination or analysis.

Immersion is a fixation technique in which the sample is immersed in fixative of volume at a minimum of 20 times greater than the volume of the tissue to be fixed. The fixative diffuses through the tissue in order to fix, so tissue size and density, as well as the type of fixative must be taken into account. Using a larger sample means it will take longer for the fixative to reach the deeper tissue.

Fixative agents can be classified as crosslinking or precipitative fixatives. Crosslinking fixatives act by creating covalent chemical bonds between proteins in tissue. This anchors soluble proteins to the cytoskeleton, and lends additional rigidity to the tissue. Precipitating, or denaturing, fixatives act by reducing the solubility of protein molecules and, often, by disrupting the hydrophobic interactions which give many proteins their tertiary structure.

One commonly used fixative in histology is the crosslinking fixative formaldehyde, which is often sold as a saturated aqueous solution under the name formalin. Formaldehyde is thought to interact primarily with the residues of the basic amino acid lysine.

Another popular aldehyde for fixation is glutaraldehyde, which is believed to operate by a similar mechanism to formaldehyde.

Formaldehyde preserves or fixes tissue or cells by crosslinking primary amino groups in proteins or nucleic acids through a —$CH_2$— linkage, i.e., a methylene bridge. Because formaldehyde is highly reactive, excessive formaldehyde in the sample or media interferes with any sample processing or analysis that involves functional proteins (such as enzymes or antibodies), nucleic acid probes, resins, or any other functional reagents with amino groups by cross-linking to these amino groups with subsequent reagent deactivation. Moreover, since the cross-links can be reversed by heat, any excessive formaldehyde in the media will eventually form cross links again, preventing cross-link reversal from being effective.

Oxidizing fixatives can react with various side chains of proteins and other biomolecules, allowing the formation of crosslinks which stabilize tissue structure. Osmium tetroxide is often used as a secondary fixative when samples are prepared for electron microscopy. Potassium dichromate, chromic acid, and potassium permanganate are also used in specific histological preparations. Two common precipitating fixatives are ethanol and methanol. Acetone is also used.

Acetic acid is a denaturant that is sometimes used in combination with other precipitating fixatives. Alcohols, by themselves, are known to cause shrinkage of tissue during fixation while acetic acid alone is associated with tissue swelling; combining the two may result in better preservation of tissue morphology. Other fixative agents include picric acid and mercuric chloride.

One of the problems with fixing biological samples is that the nucleic acids and proteins in the samples may be irreversibly bound to the fixative agent(s). Even if the nucleic acids and proteins are not irreversibly bound to the fixative agent(s), removal of excess fixative agents from the samples may be important for reliable recovery and analysis of nucleic acids and proteins. Additionally, fixative agents may interfere with the use of the isolated protein or nucleic acid in downstream biochemical analyses, such as PCR.

SUMMARY OF THE INVENTION

The present disclosure relates to methods of recovering and analyzing a target molecule, such as a nucleic acid or protein, from a fixed biological sample and materials and kits useful in such methods.

In one embodiment, a method is provided for extracting a target molecule from a biological sample preserved in a liquid cytology preservative solution.

In an embodiment, the method comprising: A) contacting the biological sample with a scavenger solution comprising a scavenging agent comprising at least one terminal hydrazine group of the formula:

and B) treating the biological sample under conditions sufficient to release the nucleic acid or protein from the biological sample; and C) recovering the target molecule from the isolation solution, wherein said target molecule is a nucleic acid or a polypeptide.

In one embodiment, the scavenging agent is selected from the group consisting of a) a compound according to formula I:

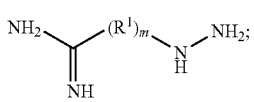

and b) a compound according to formula II:

wherein $R^1$ is selected from the group consisting of: $C_1$-$C_{12}$ alkyl; $C_1$-$C_{12}$ alkenyl; $C_3$-$C_6$ cycloalkyl; $C_3$-$C_6$ cycloalkenyl; $C_6$-$C_{10}$ aryl; and $C_6$-$C_{10}$ heteroaryl; $R^2$, which in each instance may be the same or different, is selected from the group consisting of:

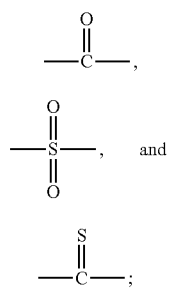

m is an integer selected from the group consisting of 0 and 1; and n is an integer selected from the group consisting of 1 and 2. In certain embodiments, the scavenging agent may be modified by methods known in the art to increase the solubility of the scavenging agent in water. For example, $R^1$ optionally may be substituted with constituents that increase the hydrophilicity of the $R^1$ constituent.

In another embodiment, the scavenging agent is a compound of formula I wherein m is 1 and $R^1$ is selected from the group consisting of $C_1$-$C_{12}$ alkyl, $C_1$-$C_6$ alkyl, and $C_2$-$C_4$ alkyl.

In another embodiment, the scavenging agent is a compound of formula II wherein n is 2, $R^1$ is selected from the group consisting of $C_1$-$C_{12}$ alkyl, $C_1$-$C_6$ alkyl, and $C_2$-$C_4$ alkyl; and $R^2$ is

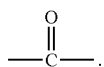

In another embodiment, the scavenging agent is selected from the group consisting of semicarbazide; thiosemicarbazide; carbazide; thiocarbazide; N-aminoguanidine and a salt thereof, including hydrochloride salts; N,N-diaminoguanidine and a salt thereof, including dihydrochloride salts; acetylhydrazide; adipic acid dihydrazide; succinic acid dihydrazide; formic hydrazide; maleic acid dihydrazide; malonic acid dihydrazide; benzenesulfonylhydrazide; tosylhydrazide; methylsulfonylhydrazide.

In another embodiment, the scavenger solution comprises from about 0.1M to about 1.0M, from about 0.1M to about 0.5M, from about 0.2M to about 0.4M, or about 0.3M of the scavenging agent.

In another embodiment, about 0.3M adipic acid dihydrazide or about 0.3M succinic acid dihydrazide is used.

In another embodiment, the scavenger solution is added directly to the liquid cytology preservative solution.

In another embodiment, the scavenger solution comprises about 2 parts by volume of the lysis solution and about 1 part by volume of the biological sample preserved in the liquid cytology preservative solution.

In another embodiment, the scavenger solution further comprises a protein digestive enzyme.

In another embodiment, the biological sample is contacted with the scavenger solution before the target molecule is released from the biological sample.

In another embodiment, the target molecule is released from the biological sample by lysing the biological sample in the presence of a lysis solution.

In another embodiment, the scavenger solution functions as the lysis solution.

In another embodiment, the scavenger solution is added to biological sample before, after, or at the same time as the lysis solution.

In another embodiment, the target molecule is a target nucleic acid and the target nucleic acid is recovered from the scavenger solution by a method comprising: (i) hybridizing a nucleic acid probe to the target nucleic acid with a second nucleic acid to form a nucleic acid hybrid; (ii) binding the nucleic acid hybrid to a solid phase; (iii) separating the solid phase from the scavenger solution; and (iv) eluting the target nucleic acid from the solid phase.

In another embodiment, the nucleic acid hybrid is a DNA: RNA hybrid.

In another embodiment, the nucleic acid hybrid is bound to the solid phase by a method comprising contacting the nucleic acid hybrid with an antibody capable of binding to the nucleic acid hybrid, wherein the antibody is bound to the solid phase or adapted to be bound to the solid phase.

In another embodiment, the target nucleic acid is eluted from the solid phase at an elution temperature of from about 20° C. to about 70° C.

In another embodiment, the target nucleic acid is eluted from the solid phase at an elution temperature of from about 50° C. to about 60° C.

In another embodiment, a lysis solution is provided, comprising:
(i) a buffer;
(ii) a detergent;
(iii) a scavenging agent comprising at least one terminal hydrazine group of the formula

and
(iv) optionally, protein digestive enzyme.

In another embodiment, the scavenging agent of the lysis solution is selected from the group consisting of:
a) a compound according to formula I:

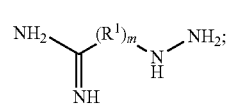

and
b) a compound according to formula II:

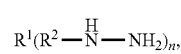

wherein:
$R^1$ is selected from the group consisting of: $C_1$-$C_{12}$ alkyl; $C_1$-$C_{12}$ alkenyl; $C_3$-$C_6$ cycloalkyl; $C_3$-$C_6$ cycloalkenyl; $C_6$-$C_{10}$ aryl; and $C_6$-$C_{10}$ heteroaryl, wherein $R^1$ is optionally substituted so as to increase the solubility of the scavenging agent in water;

$R^2$ which in each instance may be the same or different, and is selected from the group consisting of:

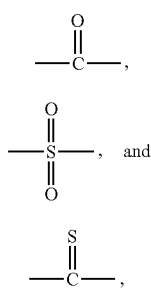

and m is an integer selected from the group consisting of 0 and 1; and n is an integer selected from the group consisting of 1 and 2.

In another embodiment, semicarbazide; thiosemicarbazide; carbazide; thiocarbazide; N-aminoguanidine and a salt thereof, including hydrochloride salts; N,N-diaminoguanidine and a salt thereof, including dihydrochloride salts; acetylhydrazide; adipic acid dihydrazide; succinic acid dihydrazide; formic hydrazide; maleic acid dihydrazide; malonic acid dihydrazide; benzenesulfonylhydrazide; tosylhydrazide; methylsulfonylhydrazide.

In another embodiment, the scavenging agent of the lysis solution is selected from the group consisting of adipic acid dihydrazide, succinic acid dihydrazide, and aminoguanidine hydrochloride.

In another embodiment, the lysis solution comprises from about 0.2M to about 1.5M of the scavenging agent.

In another embodiment, the lysis solution comprises from about 0.2M to about 0.5M adipic acid dihydrazide or from about 0.2M to about 0.5M succinic acid dihydrazide.

In another embodiment, a kit for recovering a target molecule from a biological sample preserved in a liquid cytology preservative solution is provided, said kit comprising a lysis solution as set forth above and optionally comprising at least one additional component selected from the group consisting of: protein digestive enzyme, a solid phase, a nucleic acid probe capable of hybridizing to the target nucleic acid, and an antibody.

DETAILED DESCRIPTION

Figure 1:
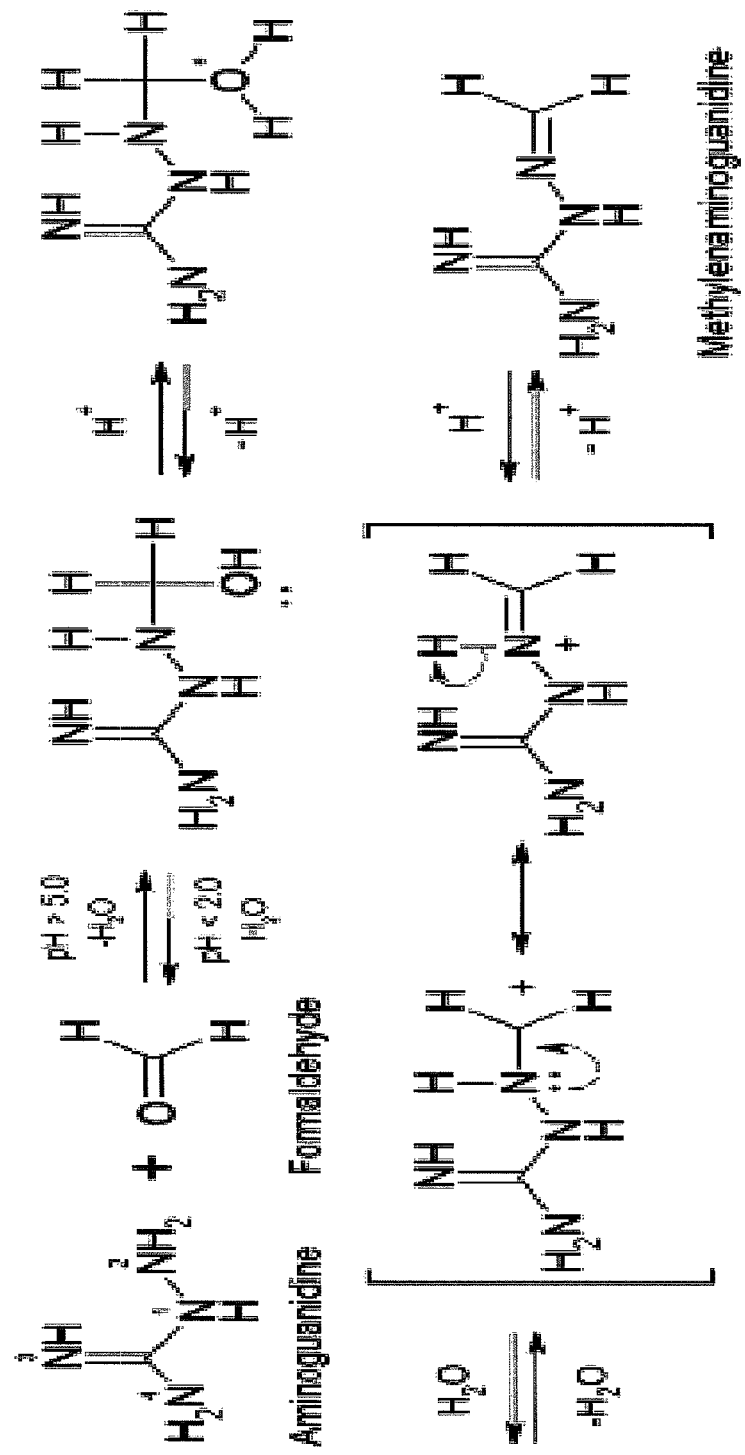
FIG. 1 outlines the basic mechanism by which hydrazines function as carbonyl scavengers, using aminoguanidine as an exemplary hydrazine compound.

The present application relates generally to the use of scavenger compounds to increase the recovery a target molecule from a biological sample preserved in a liquid cytology medium.

In an embodiment, a method is provided for recovering a nucleic acid or a protein from a biological sample in a liquid cytological preservative medium, comprising: a) adding a scavenger agent to the medium; b) incubating at a temperature and for a time sufficient for the scavenger agent to scavenge a preservative agent in the sample; and c) recovering the nucleic acid or protein. As used herein, a scavenging agent is any compound that is capable of reacting with a fixative agent, thereby removing the fixative agent from the solution. In the context of the presently disclosed materials and methods, these compounds ideally exhibit one or more of the following properties: (1) highly soluble in water; (2) chemically neutral; (3) non-toxic; and (4) readily available and inexpensive. In another embodiment, these compounds exhibit each of the above properties.

The liquid cytological preservative medium may include cross-linking and/or precipitating preservative agents. Cross-linking preservative agents include without limitation aldehydes, osmium tetroxide, potassium dichromate, chromic acid, and potassium permanganate. Precipitating preservative agents include without limitation alcohols and acetic acid.

In one embodiment, the liquid cytological preservative media comprises a carbonyl-based preservative agent, such as formaldehyde. Formaldehyde is a cross-reactive molecule that fixes cells by cross-linking amino groups by a methylene bridges. Although this is useful for cytology purposes, it can inhibit the efficient isolation of nucleic acids and/or proteins from the fixed samples.

In an embodiment, the liquid cytology preservative medium comprises a aldehyde. Exemplary aldehydes commonly used in liquid cytology preservative medium includes, but is not limited to, formaldehyde, glyoxal, glutaraldehyde, glyceraldehyde, acrolein, or other aliphatic aldehydes; or aldehyde(s) of unknown nature. One such liquid cytological preservative medium is SUREPATH®, one of the most commonly used preservative media in clinical settings. SUREPATH medium has a nearly 37% formaldehyde content and also contains methanol, ethanol, and isopropanol. The high formaldehyde content makes it a useful fixative, but poses challenges for extracting target molecules (such as nucleic acids and proteins) from the fixed samples and using them for subsequent molecular analysis. Also included in this embodiment are preservative media known to contain formaldehyde releasers, including but not limited to, Quaternium-15 (methenamine-3-chloroallylochloride), Tris Nitro (tris-hydroxymethylnitromethane), Glydant (1,3-dimethylol-5,5-dimethyl hydantoin, or DMDM-hydantoin), Germal-115 (imidazolidinyl urea), Germall II (diazolidinyl urea), Bronopol (2-bromo-2-nitropropane-1,3-diol), Bronidox (5-bromo-5-nitro-1,3-dioxane), Bromothalonil (methyldibromo glutaronitrile, 1,2-dibromo-2,4-dicyanobutane), Suttocide A (hydroxymethylglycinate), and paraformaldehyde. Also included in this embodiment are media containing aldehydes of unknown origins, which can be detected by use of aldehyde-specific reagents, such as Purpald (4-Amino-3-hydrazino-5-mercapto-1,2,4-triazole).

In one embodiment, the scavenging agent is capable of reacting with a carbonyl compound, such as an aldehyde. Exemplary carbonyl scavenging agents include, without limitation, hydrazines. As used herein, a hydrazine is any compound comprising a terminal hydrazine functional group. As used herein a "hydrazine functional group" is a chemical group according to the following formula:

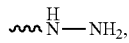

wherein the wavy bond indicates an attachment to the remainder if the chemical structure. Hydrazines readily react with carbonyls (aldehydes and ketones) to form hydrazone bonds. These bonds replace the oxygen of the carbonyl with a nitrogenous functional group limiting the ability of the aldehyde to bind with other factors. An exemplary reaction scheme is set forth in FIG. 1.

Hydrazines may be a unifunctional or multifunctional. A "unifunctional" hydrazine is a hydrazine containing a single terminal hydrazine functional group. A "multifunctional hydrazine" is a hydrazine containing more than one terminal hydrazine functional group.

In one embodiment, the scavenging agent is a hydrazine according to formula I:

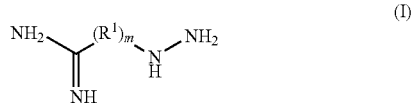

wherein:
$R^1$ $C_1$-$C_{12}$ alkyl; $C_1$-$C_{12}$ alkenyl; $C_3$-$C_6$ cycloalkyl; $C_3$-$C_6$ cycloalkenyl; $C_6$-$C_{10}$ aryl; and $C_6$-$C_{10}$ heteroaryl; and m is an integer selected from the group consisting of 0 and 1.

In one exemplary embodiment, the scavenging agent is aminoguanidine, which is a hydrazine according to formula I wherein m is 0.

In other exemplary embodiments, the scavenging agent is a hydrazine according to formula I wherein m is 1 and $R^1$ is selected from the group consisting of $C_1$-$C_{12}$ alkyl, $C_1$-$C_6$ alkyl, and $C_2$-$C_4$ alkyl.

In another embodiment, the scavenging agent is selected from the class of hydrazines known as hydrazides. Hydrazides similarly are capable of reacting with carbonyls (aldehydes and ketones) to form hydrazone bonds. As used herein, a hydrazide is a compound comprising a terminal hydrazide functional group:

wherein the wavy bond indicates an attachment to the core chemical structure and $R^2$ is selected from the group consisting of:

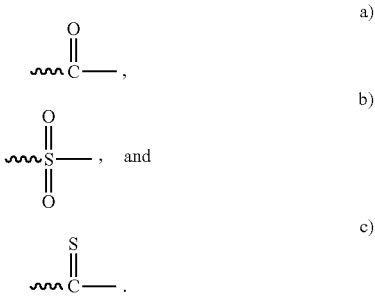

In one embodiment, the scavenging agent is a hydrazide according to formula II:

wherein:
$R^1$ $C_1$-$C_{12}$ alkyl; $C_1$-$C_{12}$ alkenyl; $C_3$-$C_6$ cycloalkyl; $C_3$-$C_6$ cycloalkenyl; $C_6$-$C_{10}$ aryl; and $C_6$-$C_{10}$ heteroaryl; wherein $R^1$ may optionally be optionally substituted so as to increase the solubility of the scavenging agent in water $R^2$ which may be in each instance the same or different and is selected from the group consisting of:

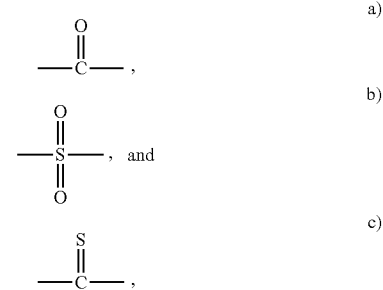

and
m is an integer selected from the group consisting of 1 and 2.

In one exemplary embodiment, the scavenging agent is a hydrazide according to formula II wherein $R^1$ is selected from the group consisting of $C_1$-$C_{12}$ alkyl, $C_1$-$C_6$ alkyl, and $C_2$-$C_4$ alkyl.

In another exemplary embodiment, the scavenging agent is a difunctional hydrazide according to formula II wherein n is 2 and $R^1$ is selected from the group consisting of $C_1$-$C_{12}$ alkyl, $C_1$-$C_6$ alkyl, and $C_2$-$C_4$ alkyl.

In another embodiment, the scavenging agent is a hydrazine is selected from carbonic and thiocarbonic acid derivatives, including but not limited to: semicarbazide (chemical formula: $NH_2C(=O)NHNH_2$); thiosemicarbazide (chemical formula: $NH_2C(=S)NHNH_2$); carbazide (chemical formula: $NH_2NHC(=O)NHNH_2$); thiocarbazide (chemical formula: $NH_2NHC(=O)NHNH_2$); N-aminoguanidine and a salt thereof, including hydrochloride salts, and N,N-diaminoguanidine (chemical formula: $NH_2NHC(=NH)NHNH_2$), and a salt thereof, including dihydrochloride salts.

In other exemplary embodiments, the scavenger agent is a hydrazine selected from the group consisting of acetylhydrazide (chemical formula: $CH_3C(=O)NHNH_2$), adipic acid dihydrazide (chemical formula: $NH_2NHC(=O)(CH_2)_4C(=O)NHNH_2$), succinic acid dihydrazide, (chemical formula: $H_2NNHCOCH_2CH_2CONHNH_2$), formic hydrazide (chemical formula: $NH_2NHC(=O)H$), maleic acid dihydrazide (chemical formula: $H_2NNHCOCHCHCONHNH_2$), and malonic acid dihydrazide (chemical formula: $H_2NNHCOCH_2CONHNH_2$).

In other exemplary embodiments, the scavenger agent is a hydrazine selected from sulfonic acids derivatives, including but not limited to, benzenesulfonylhydrazide (chemical formula: $H_2NNHS(=O)_2C_6H_5$), tosylhydrazide (chemical formula: $H_2NNHS(=O)_2C_6H_5CH_3$), and methylsulfonylhydrazide (chemical formula: $H_2NNHS(=O)_2CH_3$).

In certain embodiments, the scavenging agent may be modified by methods known in the art to increase the solubility of the scavenging agent in water. For example, $R^1$ in according to formula I or formula II optionally may be substituted with constituents that increase the hydrophilicity of the $R^1$ constituent.

In one embodiment, the method comprises contacting the biological sample with a scavenger solution. As used herein, the term "scavenger solution" refers to an aqueous solution comprising the scavenging agent. In an exemplary embodiment, the biological sample may be separated from the liquid cytology preservative medium and then contacted with the scavenger solution. In such a case, the biological sample may be incubated in a single aliquot of the scavenger solution or may be washed sequentially in the scavenger solution. In another exemplary embodiment, the scavenger solution may be added directly to the liquid cytology preservative medium. In another exemplary embodiment, the amount of scavenger solution to be added may be based on an estimation of the quantity of fixative agent in the sample. The amount of scavenging agent can be the same as the amount of fixative agent in the sample, less than the amount of the fixative agent in the sample, or in excess of the fixative agent in the sample. In one embodiment, the amount of scavenging agent is in slight excess over the amount of fixative agent in the sample. In an exemplary embodiment, the scavenger solution comprises from about 0.1M to about 1.0M, from about 0.1M to about 0.5M, from about 0.2M to about 0.4M, or about 0.3M of the scavenging agent. In another embodiment, about 0.3M adipic acid dihydrazide or succinic acid dihydrazide is used. As used herein, the term "about," when used in the context of a concentration, expressly includes all concentrations which can be rounded up or down to the indicated concentration.

In another embodiment, the target molecule may be extracted from the biological sample by a method comprising, inter alia, lysis. As used herein, the terms "lysis" and "lysing" refer to the act of disrupting the integrity of a cell wall; a cell membrane; or an organelle or other structure defined by a lipid membrane, including but not limited to an endoplasmic reticulum, Golgi apparatus, lysosome, mitochondrion, nucleus, vacuole, and vesicle. Exemplary methods of lysis include mechanical lysis, such as by sonication or cytolysis; and chemical lysis, including use of detergents such as polyoxyethyleneglycol dodecyl ether (sold commercially as Brij-58), 3-[(3-cholamidopropyl)dimethylammonio]-1-propanesulfonate (sold commercially as CHAPS), Nonidet P-40 (also known as Igepal CA-630), deoxycholate, Triton X-100, sodium dodecyl sulfate (sold commercially as SDS), and/or polysorbate surfactants (sold commercially as TWEEN).

When the target molecule is extract by lysis, the biological sample should be contacted with a lysis solution. As used herein, "lysis solution" refers to any solution that is useful for lysing a cell. Exemplary lysis solutions include without limitation hypotonic lysis solutions and detergent-based lysis solutions, including but not limited to lysis solutions comprising polyoxyethylene (20) cetyl ether (sold commercially as Brij-58), 3-[(3-cholamidopropyl)dimethylammonio]-1-propanesulfonate (sold commercially as CHAPS), Nonidet P-40 (also known as Igepal CA-630, tert-octylphenoxy poly (oxyethylene)ethanol), deoxycholate, Triton X-100, sodium dodecyl sulfate (sold commercially as SDS), and/or polysorbate surfactants (sold commercially as TWEEN).

In another embodiment, the lysis solution may optionally comprise a buffering agent. Exemplary buffering agents include without limitation tris(hydroxymethyl)aminomethane ("TRIS") and derivatives thereof, such as N-tris-(hydroxymethyl)methyl-3-aminopropanesulfonic acid ("TAPS"), 3-[N-tris-(hydroxymethyl)-methyl-amino]-2-hydroxypropanesulfonic acid ("TAPSO"); N-tris(hydroxymethyl)methyl-2-aminoethanesulfonic acid ("TES"); N-[tris (hydroxymethyl)methyl]-glycine ("TRICINE"); bis(2-hydroxyethyl)iminotris-(hydroxymethyl)methane ("bis-TRIS"); 1,3-bis[tris(hydroxy-methyl)methylamino]propane ("bis-TRIS PROPANE"); carbonate-bicarbonate; glycine; phosphate; 4-(2-hydroxyethyl)-1-piperazineethanesulfonic acid ("HEPES"); N,N-bis(2-hydroxyethyl)glycine ("Bicine"); 3-(N-morpholino)propanesulfonic acid ("MOPS"); and other Good buffers. Numerous other constituents of the lysis solution may be included as well. The precise type and formulation of the lysis solution can be readily determined by a person having ordinary skill in the art according to the sample type, the method of lysis, the analyte of interest, and the method of analysis to be used.

In an embodiment, the scavenger solution may also function as the lysis solution. Alternatively, the scavenger solution and the lysis solution may be added to the biological sample as separate solutions, either sequentially or at the same time. In one embodiment, the biological sample is incubated with the scavenger solution before the lysis solution is added. In another embodiment, the scavenger solution is removed before the lysis solution is added. In another embodiment, the lysis solution is added to the biological sample before the scavenger solution is added. In another embodiment, the biological sample may be incubated with the lysis solution under conditions sufficient to either partially or completely release the target molecule from the biological sample before the scavenger solution is added.

In one embodiment, the target molecule is a nucleic acid. Any method may be used to recover the nucleic acid from the biological sample. By way of example, methods of recovering the target nucleic acid include without limitation: chromatography, including but not limited to silica or glass adsorption, ion exchange chromatography, affinity purification, spin column chromatography, and gel filtration; solvent extraction and precipitation; and centrifugation. Nucleic acid recovery methods include without limitation ammonium sulfate precipitation, differential solubilization, sucrose gradient centrifugation, and chromatography. By way of example and not limitation, the nucleic acid may be isolated by using magnetic beads modified to bind specifically to nucleic acids.

In another embodiment, a nucleic acid comprising a specific sequence may be isolated by hybridizing it to a nucleic acid probe complementary to the specific sequence. In one embodiment, the nucleic acid probe is bound to a solid phase or adapted to be bound to a solid phase. In another embodiment, hybridization of the nucleic acid probe to the nucleic acid molecule results in a DNA:RNA hybrid between the probe and the nucleic acid molecule. The resulting hybrid may then be bound by an antibodies known to bind specifically to DNA:RNA hybrids ("DNA:RNA-binding antibody"), which in turn may be bound to a solid phase or adapted to be bound to a solid phase. In either case, hybridization of the probe with the nucleic acid results in the nucleic acid being associated with a solid phase, which may then be separated from the lysate using mechanical means. By way of example and not limitation, such methods are described in U.S. Pat. No. 6,228,578 and U.S. patent application Ser. No. 12/695,071, the contents of which are incorporated in their entirety by reference. Exemplary DNA:RNA-binding antibodies include, but are not limited to, those disclosed in U.S. Pat. Nos. 4,732,847 and 4,865,980, the contents of which are incorporated herein by reference in their entireties.

By way of example, and not limitation, an appropriate solid phase includes, but is not limited to: silica, borosilicates, silicates, anorganic glasses, organic polymers such as poly (meth)acrylates, polyurethanes, polystyrene, agarose, polysaccharides such as cellulose, metal oxides such as aluminum oxide, magnesium oxide, titanium oxide and zirconium oxide, metals such as gold or platinum, agarose, sephadex, sepharose, polyacrylamide, divinylbenzene polymers, styrene divinylbenzene polymers, dextrans, and derivatives thereof, and/or silica gels, beads, membranes, and resins; glass or silica surfaces, such as beads, plates, and capillary tubes; magnetizable or magnetic (e.g. paramagnetic, superparamagnetic, ferromagnetic or ferrimagnetic) particles, including but not limited to polystyrene, agarose, polyacrylamide, dextran, and/or silica materials having a magnetic material incorporated therein or associated therewith. In some exemplary embodiments, the nucleic acid probe or antibody can be linked to the surface of a processing vessel such as a micro-tube, a well of micro-plate, or capillary, and using these surfaces the nucleic acid can be isolated on a micro scale. Where a biotinylated nucleic acid probe or antibody is provided, the solid phase may be coated with a substance capable of binding the biotin moiety, such as, for example, avidin, streptavidin, and/or neutravidin. In another embodiment, the solid phase may be coated with, or adapted to be coated with, an antibody specific for a DNA:RNA hybrid.

Nucleic acids obtained using the disclosed methods and compositions may be used in subsequent molecular analytical methods including without limitation gel electrophoresis, PCR-related techniques including reverse transcriptase PCR and real time PCR, sequencing, sub-cloning procedures, Southern blotting, northern blotting, fluorescent in situ hybridization, and various mutational analyses including hybrid capture and multiplex analysis.

In one embodiment, the scavenger solution comprises all components necessary for releasing the target nucleic acid from the biological sample and isolating the target molecule. By way of example and not limitation, such a scavenger solution could comprise, inter alia, a detergent, a buffer, a nucleic acid probe specific for the target nucleic acid, and a solid phase, wherein hybridization of the nucleic acid to the nucleic acid probe captures the target nucleic acid to the solid phase. By way of example and not limitation, this could be achieved by modifying the nucleic acid probe to comprise a ligand capable of binding to a constituent of the solid phase. For example, the probe may be modified to contain a biotin moiety and the solid phase may be coated with a substance capable of binding the biotin moiety, such as, for example, avidin, streptavidin, and/or neutravidin, or a fragment thereof. In another example, hybridization of the target nucleic acid to the nucleic acid probe may form a DNA:RNA hybrid, which then may be captured to the solid phase via antibodies specific for DNA:RNA hybrids, such as by the methods described in U.S. Pat. No. 6,228,578 and U.S. patent application Ser. No. 12/695,071, the contents of which are incorporated in their entirety by reference.

In one embodiment, the target molecule is a polypeptide. As used herein, the term "polypeptide" refers to any molecule comprising at least two amino acids joined by a peptide bond, and expressly includes oligopeptides and proteins. Polypeptide recovery methods include without limitation ammonium sulfate precipitation, differential solubilization, sucrose gradient centrifugation, and chromatography. Chromatographic polypeptide isolation methods include without limitation size exclusion, ion exchange, hydrophobic interaction, affinity, immuno-affinity, and metal binding chromatography.

Polypeptides obtained with the disclosed methods and compositions may be used in subsequent molecular analytical methods including without limitation sequencing, immuno-precipitation, western blots, ELISA assays, dot blots, and enzyme assay The methods described also can be used to isolate whole pathogens, including without limitation bacteria, fungi, yeast, protozoa, prions, and viruses.

The methods and compositions described herein are easily and rapidly optimized for specimens preserved in either cross-linking or precipitating fixatives. The methods and compositions described herein also are adaptable for all biological fluids and provide simple protocols that are proven compatible with high throughput automation, including for example the QIAensemble® Next Gen™ Sample Processor, an automated sample processing device for extraction and analysis which provides full automation, including de-capping and capping of specimens and zero ergonomic movements. As such, they provide ultra high through-put and ecologically friendly sample processing by allowing for a flexible input volume, non-hazardous material liquid waste, limited solid waste, and reagents that may be stored at room temperature.

EXAMPLES

Materials and Methods
  A. Cells and Samples
  Biological samples comprising human papillomavirus 16 nucleic acids were used to test the materials and methods according to the present disclosure. In some examples, a SiHa cell line is used, which are derived from a human cervical carcinoma. SiHa cells are known to contain an integrated HPV 16 genome. In other examples, clinical samples determined to be infected with HPV 16 were used. As negative controls for the HPV 16 assay, Jurkat cells or clinical samples determined to be HPV negative were used.

Unless otherwise indicated, all samples used in the present examples were fixed at least overnight in the indicated liquid cytology preservative medium.
B. General Protocol: HandyLabs™ Extraction
  In some examples, extraction was performed using the HandyLabs™ extraction technology, which is a commercially available DNA extraction technology based on anion exchange chromatography, using paramagnetic beads treated with an anion exchange material.

The following general protocol was used in the present examples.

Samples were spiked in 500 μL SurePath® liquid cytological medium and placed in 5 mL tubes. 100 μL of an aqueous solution of the scavenging agent (or ultrapure water) and a proteinase K tablet (provided with the kit) were added to the tube. 1.2 mL of lysis buffer and 60 μL of HL beads (both provided with the kit) were then added and tube was incubated at 60° C. for 10 minutes. A magnet was then added for 2 minutes to pellet the beads and the supernatant removed. The beads were then resuspended in 400 μL of buffer 1 (supplied with the kit), the mixture shaken, the beads pelleted, and the supernatant removed. Then, the beads were resuspended in 30 μL of buffer 2 (supplied with the kit) and the nucleic acid eluted 65.8° C. for 9 minutes. Beads were pelleted again and the eluate transferred to a 96 well plate. 12 μL of buffer 3 (supplied with the kit) and 8 μL of Digene Collection Medium (Qiagen Gaithersburg, Inc., Qiagen, MD) were added to each well. The presence of HPV 16 was detected using either the NexGen® (described in, inter alia, U.S.) or HC2® assay (described in U.S. Pat. No. 6,228,578).

C. General Protocol: QiaAmp® Extraction

In some examples, nucleic acid extraction was performed using a QiaAmp® DNA extraction kit (Qiagen Inc., Hilden, Germany), which is a commercially available DNA extraction technology based on silica gel absorption in a column format.

250 μl of a SurePath® sample and 50 μL of an aqueous solution of the scavenging agent (or ultrapure water) were added to a 2 mL tube and briefly vortexed to mix. 80 μL of buffer ATL (provided with the kit) and 20 μL of a proteinase K solution (provided with the kit) were added to the tube, the tube was pulse vortexed 10 times, and then incubated at 70° C. in a shaking water bath (900 rpm) for 15 minutes. 360 μL of 100% ethanol was added, the tube was pulse vortexed 15 times, and the mixture was incubated at room temperature for 5 minutes. The lysate was then transferred to a QiaAmp® column placed on a QiaVac® vacuum manifold. The lysate was then pulled through the column by application of vacuum. The column was then washed twice, first with 750 μL of buffer AW2 (provided with the kit) and then with 100% ethanol. Columns were then removed from the manifold, placed in 2 mL tubes, and centrifuged at 14000 rpm for 3 minutes. The columns are then placed in elution tubes and dried at 56° C. for 3 minutes. 70 μL of buffer AVE were then added to the membrane, incubated at room temperature for 5 minutes, and centrifuged at 14000 rpm for 1 minute. The eluate was transferred to a 96 well plate and the presence of HPV 16 was detected using either the NexGen® (described in, inter alia, U.S. Patent Application Publication No. 2010/0105060 A1) or HC2® assay (described in U.S. Pat. No. 6,228,578).

Example 1

In this example, the initial feasibility of using hydrazine compounds is carried out using SUREPATH clinical negatives spiked with 10,000 SiHa cells (HPV16+). Samples comprising only the clinical negatives are used as negative controls for each condition. Each sample was treated with adipic acid, lysed, and processed for nucleic acid isolation using the HandyLabs protocol set forth above. Unless otherwise indicated, each sample contains proteinase K.

As set forth in Table I, "CV" refers to the coefficient of variation, "S/N" refers to the signal to noise ratio, "RLU/CO" refers to the Relative light units/cutoff ratio, and "PK" refers to proteinase K. 1 pg of a plasmid comprising the entire HPV 16 genome was used as a positive control for the NexGen® assay. The baseline for percent recovery is established using SiHa cells spiked in Jurkat cells without a liquid cytology preservative medium. "% Recovery A" represents data obtained using 0.3M adipic acid dihydrazide without proteinase K compared to the baseline. "% Recovery B" represents data obtained using 0.3M adipic acid dihydrazide with proteinase K compared to the baseline. "% Recovery C" represents data obtained using 0.16M adipic acid dihydrazide with proteinase K compared to the baseline. "% Recovery D" represents data obtained using 0.3M adipic acid dihydrazide without proteinase K compared to the baseline.

TABLE 1

| Target | Probe B + 15 ng | | | | Avg | CV | S/N | S-N | |
|---|---|---|---|---|---|---|---|---|---|
| Negative Calibration | 53 | 55 | 53 | 59 | 55 | 5% | | | |
| Detection Reagent 1 | 39 | 41 | 41 | 45 | 42 | 6% | 0.8 | −14 | |
| HPV 16-1 pg | 275 | 263 | 301 | 289 | 282 | 6% | 5.1 | 227 | |
| | Direct Controls | | | | Avg | CV | S/N | S-N | RLU/CO |
| Jurkat | 63 | 59 | 55 | 55 | 58 | 7% | 1.0 | 0 | 0.21 |
| 20K SiHa/500 μl | 1453 | 5151 | 2067 | 941 | 2403 | 79% | 41.4 | 2345 | 8.52 |
| 0.3M Adipic Acid | 0.05M (Final) without PK | | | | Avg | CV | S/N | S-N | RLU/CO |
| Negative Clinical | 145 | 51 | 87 | | 94 | 50% | 1.0 | 0 | 0.33 |
| 20K SiHa/500 μl | 117 | 121 | 121 | | 120 | 2% | 1.3 | 25 | 0.4 |
| 0.3M Adipic Acid | 0.05M (Final) with PK | | | | Avg | CV | S/N | S-N | RLU/CO |
| Negative Clinical | 63 | 77 | 93 | | 78 | 19% | 1.0 | 0 | 0.28 |
| 20K SiHa/500 μl | 2525 | 2845 | 2579 | | 2650 | 6% | 34.1 | 2572 | 9.4 |

TABLE 1-continued

| 0.16M Adipic Acid | 0.027M (Final) with PK | | | Avg | CV | S/N | S-N | RLU/CO |
|---|---|---|---|---|---|---|---|---|
| Negative Clinical | 57 | 79 | 67 | 68 | 16% | 1.0 | 0 | 0.24 |
| 20K SiHa/500 µl | 2511 | 2655 | 2447 | 2538 | 4% | 37.5 | 2470 | 9.0 |

| 0.0M Adipic Acid | 0.0M (Final) wth PK | | | Avg | CV | S/N | S-N | RLU/CO |
|---|---|---|---|---|---|---|---|---|
| Negative Clinical | 53 | 65 | 69 | 62 | 13% | 1.0 | 0 | 0.22 |
| 20K SiHa/500 µl | 1673 | 2081 | 1997 | 1917 | 11% | 30.8 | 1855 | 6.8 |

| % Recovery A | % Recovery B | % Recovery C | % Recovery D |
|---|---|---|---|
| 1% | 110% | 105% | 79% |

Example 2

When amino guanidine hydrochloride is used as a scavenger agent in SUREPATH media with pre-incubation period of 10 minutes, 95% to 100% recovery of DNA is obtained.

TABLE 2

| | | | 500 µl of water or SP | water | water | SP | SP | SP | SP | SP | SP |
|---|---|---|---|---|---|---|---|---|---|---|---|
| | | | 0.5M Aminoguanidine | 500 µl | 500 µl | 100 µl | 100 µl | 200 µl | 300 µl | 400 µl | 500 µl |
| | | | LB (1:2) µl | 2000 | 2000 | 1200 | 1200 | 1400 | 1600 | 1800 | 2000 |
| | | | Total vol. | 3000 | 3000 | 1800 | 1800 | 2100 | 2400 | 2700 | 3000 |
| | | | PK (20 mg/ml) µl | 15 | 20 | 0 | 12 | 14 | 16 | 18 | 20 |
| | NP-SP | Negative Pool SurePath | Sp-SP | Spiked SurePath | 25000 SiHa cells spiked into 0.5 ml of negative SP pool. Cells fixed for 10 days. Final cell vol. was 0.5 ml of SP or water. Each tube extracted using anion exchange bead method. 5K cells used per well. | | | | | | |
| | 1 | 2 | 3 | 4 | 5 | 6 | 7 | 8 | 9 | 10 | 11 | 12 |
| A | DCM-NC | DCM-Ju | DCM-NC | DCM-Ju | NP-SP | NP-SP | NP-SP | NP-SP | NP-SP | NP-SP | NP-SP | NP-SP |
| B | DCM-NC | DCM-Ju | DCM-NC | DCM-Ju | NP-SP | NP-SP | NP-SP | NP-SP | NP-SP | NP-SP | NP-SP | NP-SP |
| C | DCM-NC | DCM-Ju | DCM-NC | DCM-Ju | NP-SP | NP-SP | NP-SP | NP-SP | NP-SP | NP-SP | NP-SP | NP-SP |
| D | DCM-NC | DCM-Ju | DCM-NC | DCM-Ju | NP-SP | NP-SP | NP-SP | NP-SP | NP-SP | NP-SP | NP-SP | NP-SP |
| E | DCM-1PG | DCM-Si | DCM-1PG | DCM-Si | Sp-SP | Sp-SP | Sp-SP | Sp-SP | Sp-SP | Sp-SP | Sp-SP | Sp-SP |
| F | DCM-1PG | DCM-Si | DCM-1PG | DCM-Si | Sp-SP | Sp-SP | Sp-SP | Sp-SP | Sp-SP | Sp-SP | Sp-SP | Sp-SP |
| G | DCM-1PG | DCM-Si | DCM-1PG | DCM-Si | Sp-SP | Sp-SP | Sp-SP | Sp-SP | Sp-SP | Sp-SP | Sp-SP | Sp-SP |
| H | DCM-1PG Calibrator | DCM-Si Cell Ctrl | DCM-1PG Calibrator | DCM-Si Cell Ctrl | Sp-SP | Sp-SP | Sp-SP | Sp-SP | Sp-SP | Sp-SP | Sp-SP | Sp-SP |
| | 1 | 2 | 3 | 4 | 5 | 6 | 7 | 8 | 9 | 10 | 11 | 12 |
| A | 147* | 73 | 165* | 99 | 77 | 69 | 95 | 179 | 87 | 91 | 101 | 75 |
| B | 95 | 79 | 97 | 97 | 117 | 69 | 103 | 99 | 113 | 79 | 85 | 87 |
| C | 93 | 67 | 115 | 109 | 107 | 91 | 107 | 97 | 97 | 79 | 81 | 81 |
| D | 77 | 81 | 105 | 95 | 105 | 91 | 315* | 87 | 123* | 99 | 101 | 83 |
| E | 417 | 1049 | 403 | 353 | 155 | 945 | 1095 | 913 | 953 | 1021 | 1079 | 487 |
| F | 405 | 919 | 413 | 313 | 187 | 1175 | 1081 | 883 | 927 | 1021 | 975 | 461 |
| G | 395 | 835 | 429 | 285 | 133 | 891 | 947 | 1239* | 763 | 847 | 1021 | 645 |
| H | 423 | 891 | 337 | 271 | 189 | 1083 | 1047 | 923 | 887 | 989 | 1077 | 713 |
| Avg (A-D) | 88.33 | 75 | 105.7 | 100 | 101.5 | 80 | 101.7 | 94.3 | 99 | 87 | 92 | 81.5 |
| CV (A-D) | 11.2 | 8.4 | 8.5 | 6.2 | 16.9 | 15.9 | 6 | 6.8 | 13.2 | 11.3 | 11.4 | 6.1 |

TABLE 2-continued

| | | | | | | | | | | | | |
|---|---|---|---|---|---|---|---|---|---|---|---|---|
| Avg (E-H) | 410 | 923.5 | 395.5 | 305.5 | 166 | 1023.5 | 1042.5 | 906.3 | 882.5 | 969.5 | 1038 | 576.5 |
| CV (E-H) | 3 | 9.8 | 10.2 | 11.8 | 16.2 | 12.6 | 6.4 | 2.3 | 9.5 | 8.6 | 4.8 | 21.1 |
| SN | 4.6 | 12.3 | 3.7 | 3.1 | 1.6 | 12.8 | 10.3 | 9.6 | 8.9 | 11.1 | 11.3 | 7.1 |
| % Recovery to DCM/SiHA [Shaded/Col. 2, Avg. (E-H)] | | | | | 18.0% | 110.8% | 112.9% | 98.1% | 95.6% | 105.0% | 112.4% | 62.4% |
| % Recovery to 1PG [Shaded/Col. 1, Avg. (E-H)] | | | | | 40.5% | 249.6% | 254.3% | 221.0% | 215.2% | 236.5% | 253.2% | 140.6% |
| % Recovery to DCM/SiHa [Shaded/Col. 4, Avg. (E-H)] | | | | | 54.3% | 335.0% | 341.2% | 296.7% | 288.9% | 317.3% | 339.8% | 188.7% |
| % Recovery to 1PG [Shaded/Col. 3, Avg. (E-H)] | | | | | 42.0% | 258.8% | 263.6% | 229.2% | 223.1% | 245.1% | 262.5% | 145.8% |
| % recovery-2 | | | | | 42.83 | 33.08 | 17.98 | 110.83 | 112.89 | 98.14 | 95.56 | 104.98 |
| % recovery-12 | | | | | 38.1 | 29.43 | 15.99 | 98.6 | 100.43 | 87.32 | 85.02 | 93.4 |

When amino guanidine hydrochloride is added, the solution can be thoroughly mixed. The SUREPATH specimen can be at room temperature before mixing with amino guanidine hydrochloride. Approximately 300 µL to 400 µL of amino guanidine hydrochloride (0.5M) can be added to about 500 µL of SUREPATH media used in assays described herein. If it is beneficial to reduce working volume, amino guanidine hydrochloride at higher concentration can be used. Since amino guanidine hydrochloride is highly soluble a concentrated (e.g., 4M) solution can be prepared. In an embodiment, a stock scavenger solution comprising 1M, 2M, 3M, or 4M amino guanidine hydrochloride can be used.

As set forth in Table 2, "CV" refers to the coefficient of variation, "NC" refers to negative calibration, "PK" refers to proteinase K, "DCM" refers to the DIGENE collection medium, "DCM-1PG" refers to the DIGENE collection medium with 1 pg of positive calibrator, "SP" refers to SURE-PATH media, "NP-SP" refers to Negative Pool SUREPATH media, and "Sp-SP" refers to Spiked SUREPATH media.

Example 3

Figure 2:
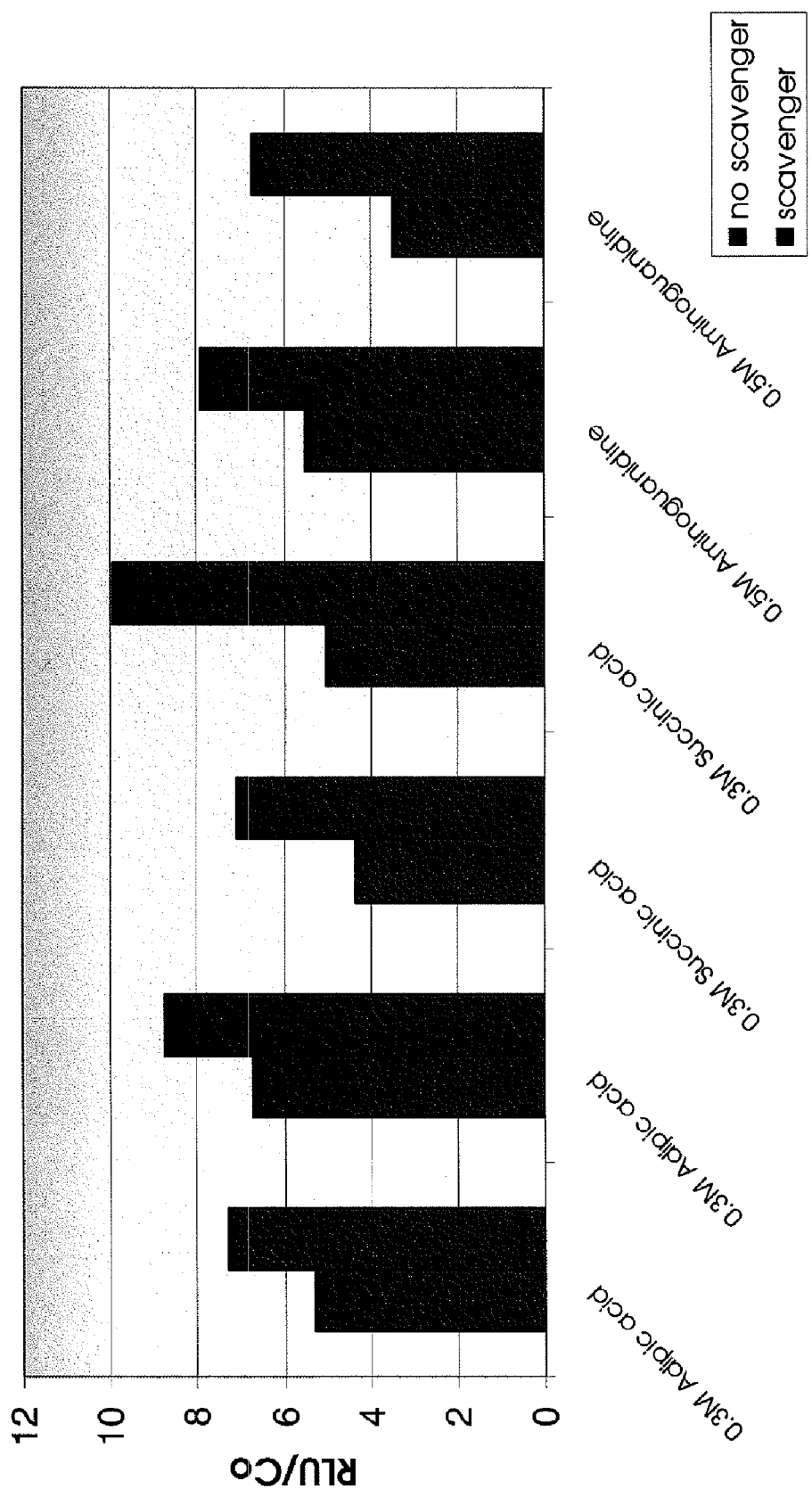
FIG. 2 illustrates the recovery of a nucleic acid from SiHa cells spiked in SurePath liquid cytological collection medium in the presence or absence of three different hydrazines: adipic acid dihydrazide, succinic acid dihydrazide, and amino guanidine. In each instance, the right bar represents the result of adding the indicated hydrazine to the indicated final concentration, while the left bar represents the result of adding an equal volume of water. The results of duplicate experiments are shown.

Aminoguanidine, adipic acid dihydrazide, and succinic dihydrazide were compared to one another in the HandyLabs protocol. 20,000 SiHa cells were spiked in either SurePath medium or Digene Collection Medium and processed according to the HandyLabs protocol set forth above. Duplicate experiments were performed for each condition. Results for each hydrazine in SurePath medium are illustrated at FIG. 2. As can be seen, in each case the addition of scavenger improved recovery of the nucleic acid. When compared to a sample in Digene Collection Medium, percent recovery in the absence of scavenger varied between 40% and 60%, while addition of the scavenger improved recovery to between 85% and 100%.

Example 4

Various concentrations of succinic acid dihydrazide and adipic acid dihydrazide were also tested in the HandyLabs protocol.

Figure 3:
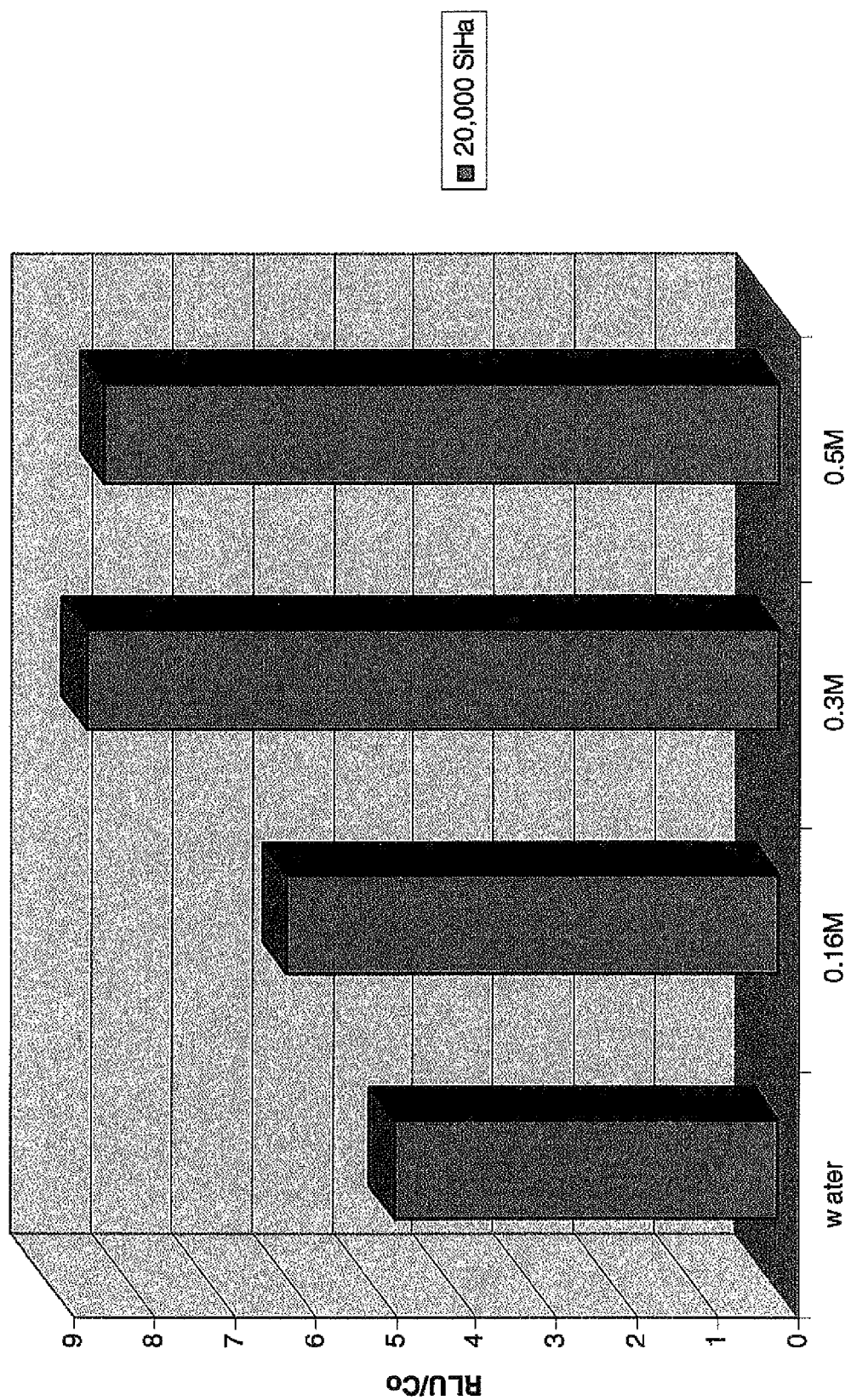
FIG. 3 demonstrates the effect of varying succinic acid dihydrazide concentration.

In one experiment, 20,000 SiHa cells were spiked into SurePath medium and processed according to the HandyLabs protocol set forth above, using 0.16M, 0.3M, or 0.5M succinic acid dihydrazide or an equal volume of water. Results are demonstrated at FIG. 3.

Figure 4:
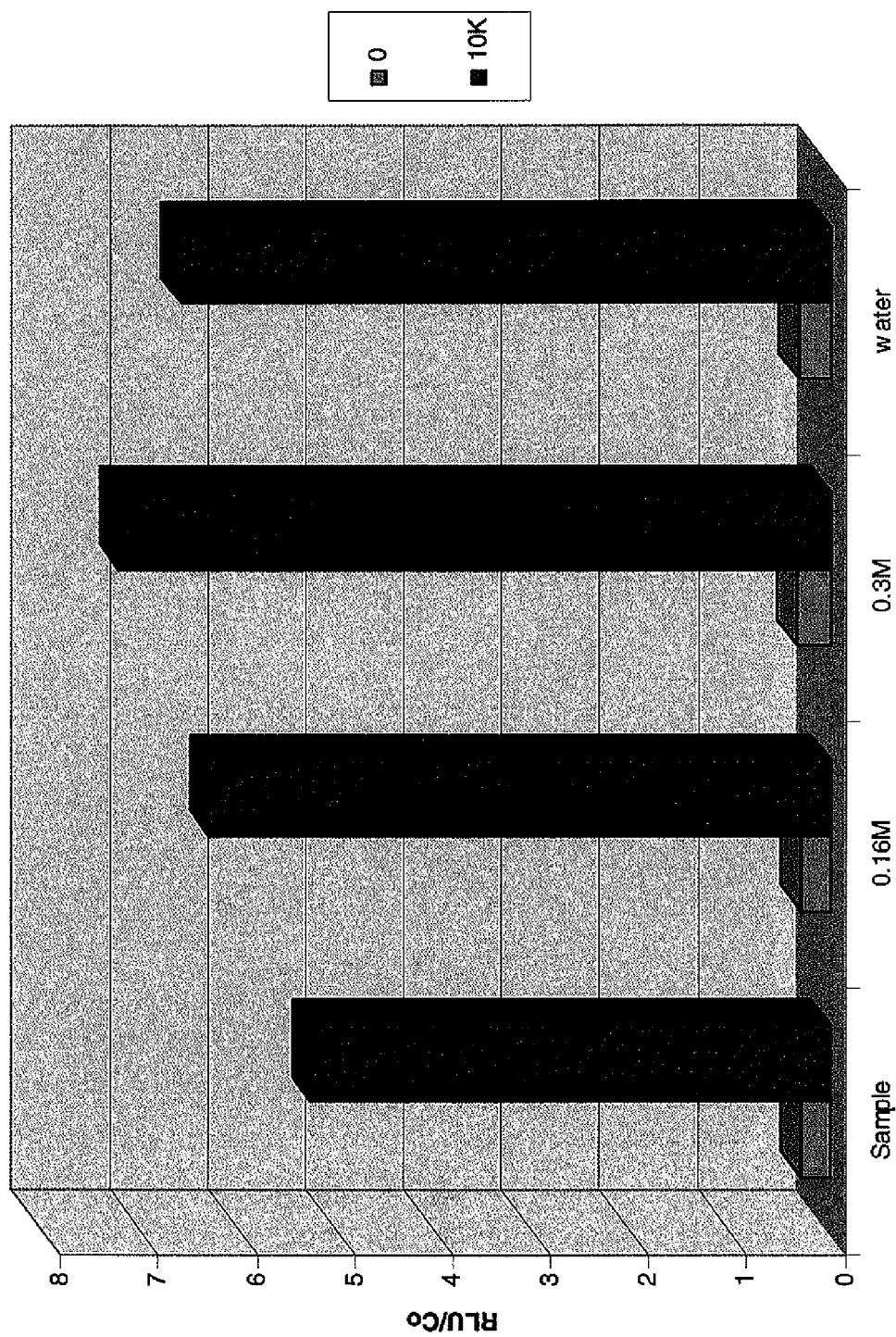
FIG. 4 demonstrates the effect of varying the concentration of adipic acid dihydrazide on samples in SurePath medium. For each condition, the left bar represents data in the absence of cells, while the right bar represents data obtained with 10,000 SiHa cells. "Sample" indicates SurePath medium alone. "0.16M" and "0.30M" indicate that the lysis buffer comprising adipic acid dihydrazide was added to the SurePath sample to a final concentration of 0.16M and 0.30M, respectively. "Water" indicates that water was used in place of SurePath.

In another experiment, 20,000 SiHa cells were spiked into SurePath medium and processed according to the HandyLabs protocol set forth above, using 0.16M, 0.3M, or 0.5M adipic acid dihydrazide or an equal volume of water. Results are demonstrated at FIG. 4.

Example 5

Figure 5:
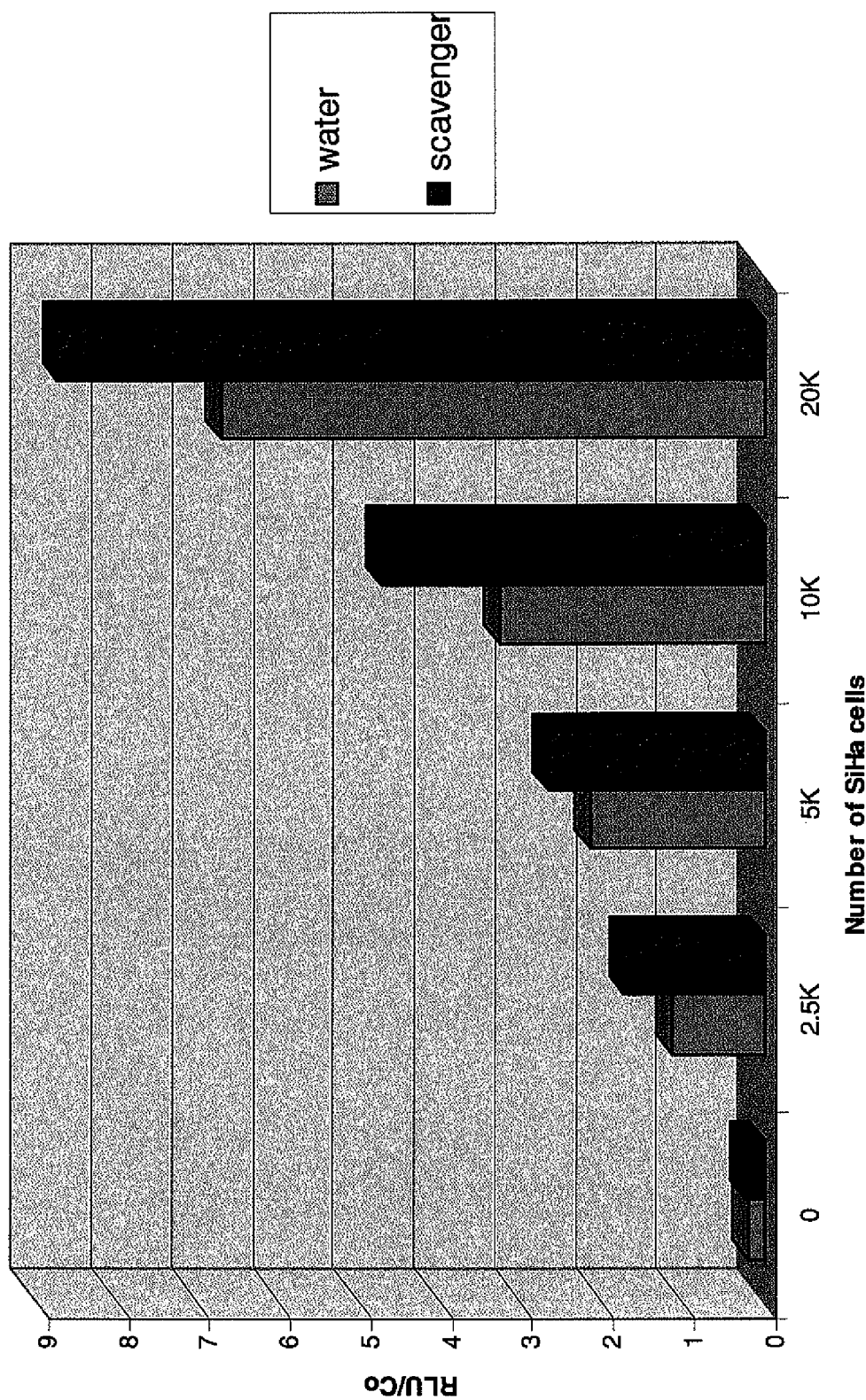
FIG. 5 demonstrates the effectiveness of adipic acid dihydrazide as a scavenger when the cell number is varied.

The effect of varying the cell number (and therefore the copy number of the target nucleic acid) was also tested. Stocks of 20,000, 10,000, 5,000, 2,500, and 0 SiHa cells per 500 µL of SurePath were generated and processed according to the HandyLabs protocol using either 0.3M adipic acid dihydrazide or an equal volume of water. Results are shown at FIG. 5.

Example 6

Figure 6:
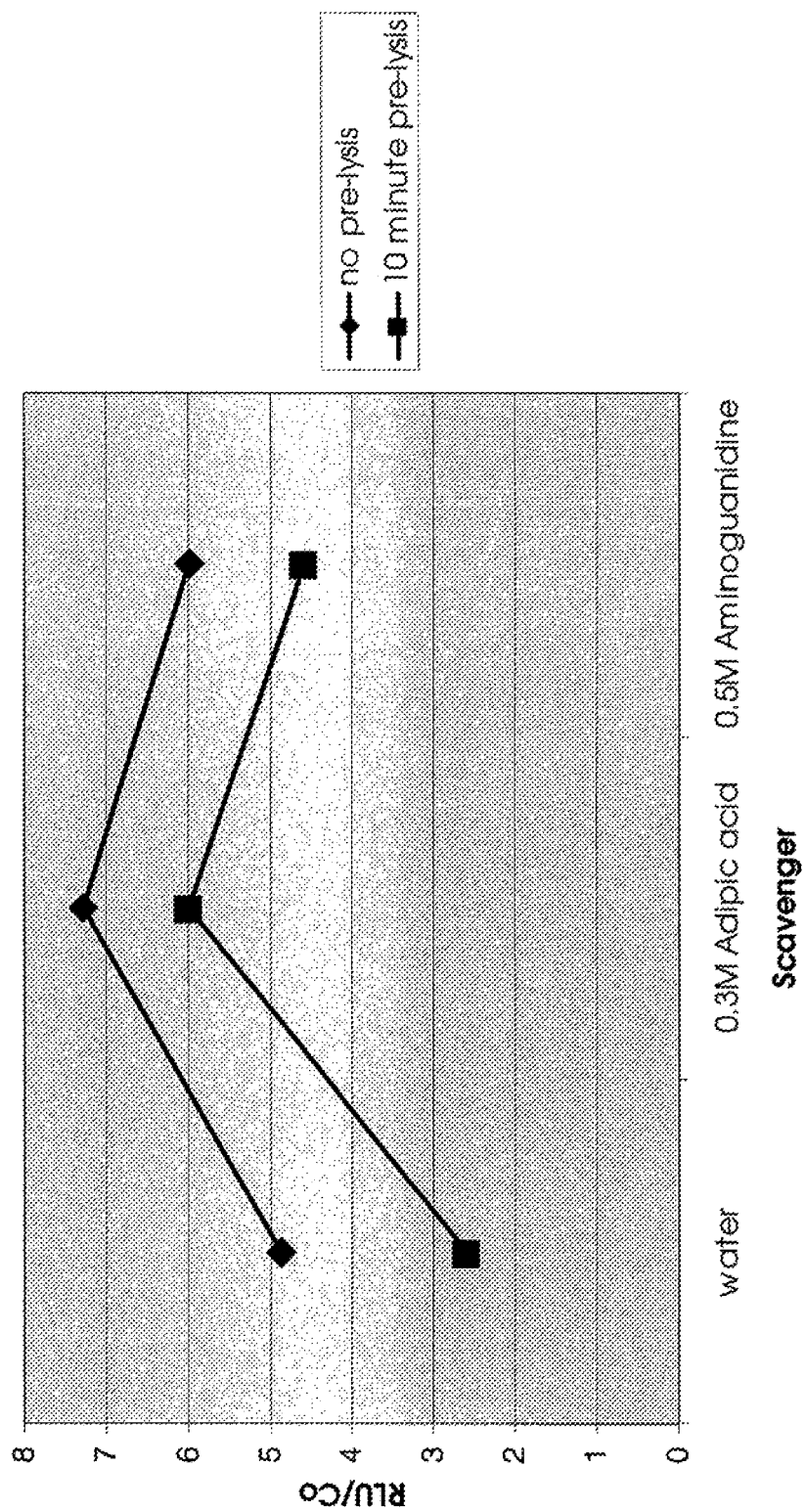
FIG. 6 illustrates the effect of a 10 minute preincubation of the biological sample with a hydrazine prior to lysis.
Figure 7:
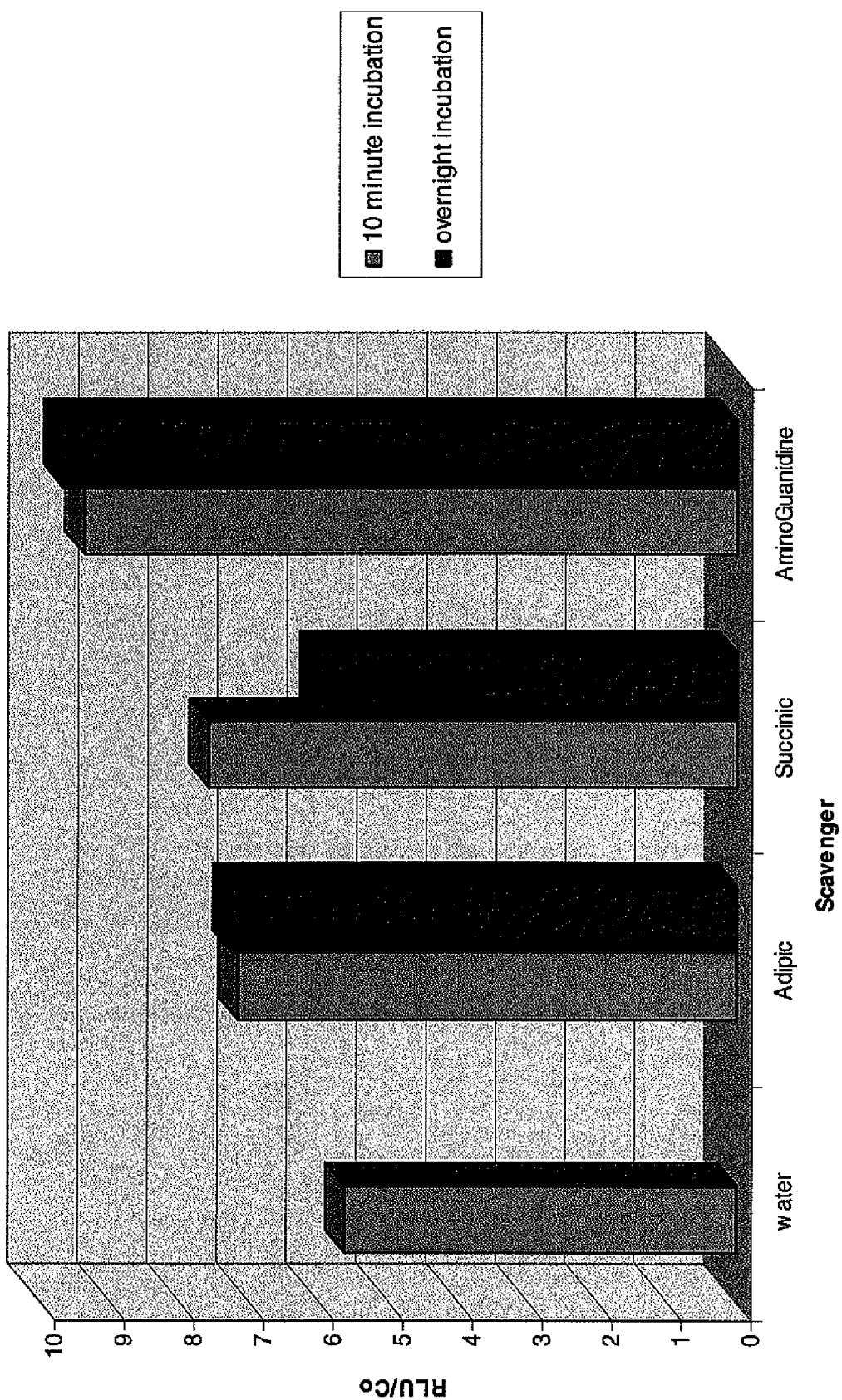
FIG. 7 compares adipic acid dihydrazide, succinic acid dihydrazide, and aminoguanidine with 10 minute and overnight treatments.

Whether pretreatment with a scavenging agent improves recovery was also tested. 20,000 SiHa cells were spiked into either SurePath medium or Digene Collection Medium and processed according to the HandyLabs protocol set forth above, except that some samples were incubated with either 0.3M adipic acid dihydrazide or 0.5M aminoguanidine (or an equal volume of water) for 10 minutes before addition of the proteinase K and lysis buffer. This was repeated using either 10 minute or overnight preincubation with 0.3M adipic acid dihydrazide, 0.3M succinic acid dihydrazide, or 0.5M aminoguanidine. Results are demonstrated at FIG. 6 and FIG. 7.

Figure 8:
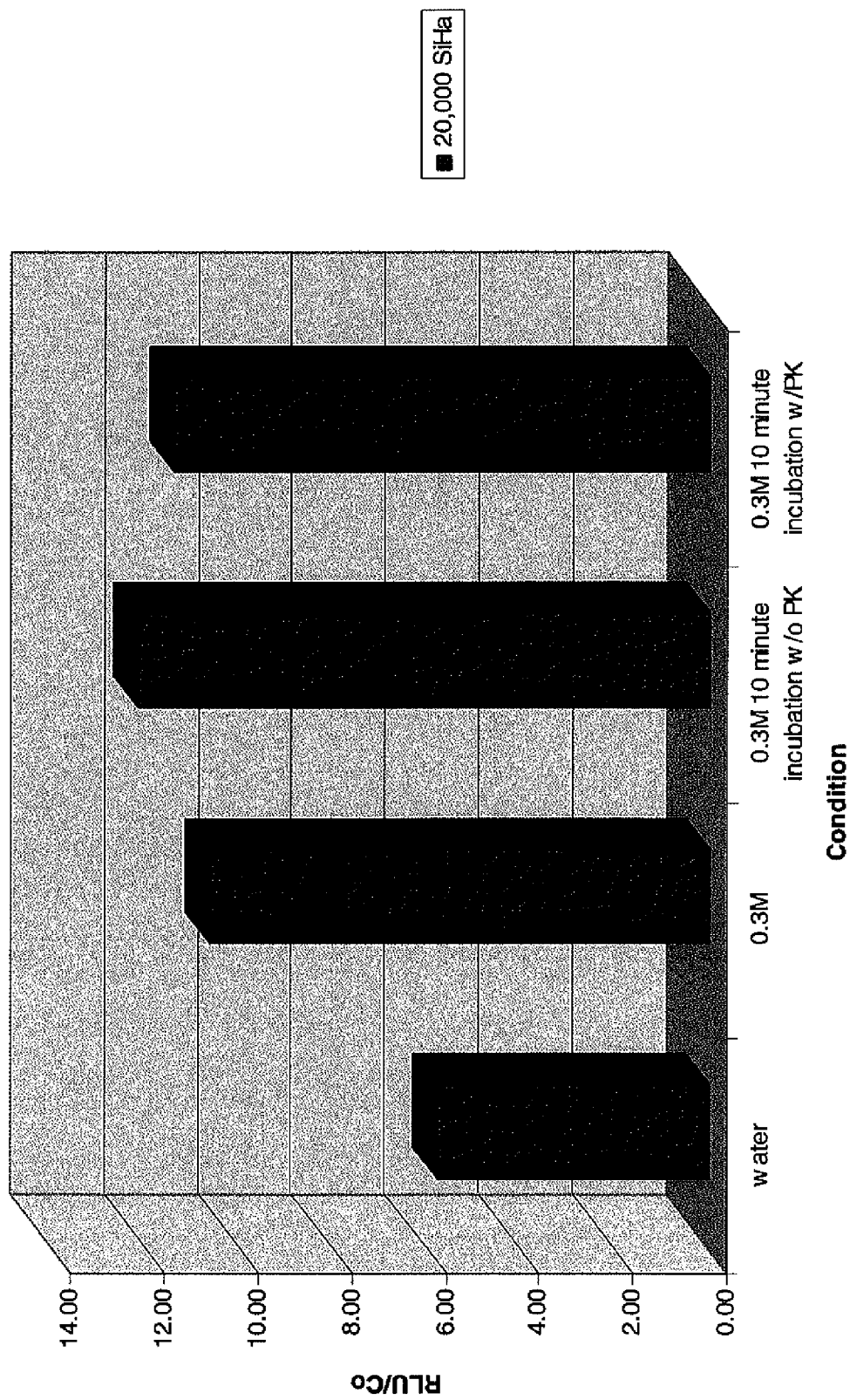
FIG. 8 demonstrates the effect of pretreatment with a hydrazine in the presence or absence of proteinase K.

Additionally, it was tested whether inclusion of proteinase K in the pretreatment would have an effect. Samples were tested as above using 0.3M succinic acid dihydrazide as the scavenger, except one sample was pretreated for 10 minutes with a scavenger solution comprising proteinase K. Results are shown at FIG. 8.

Example 7

Figure 9:
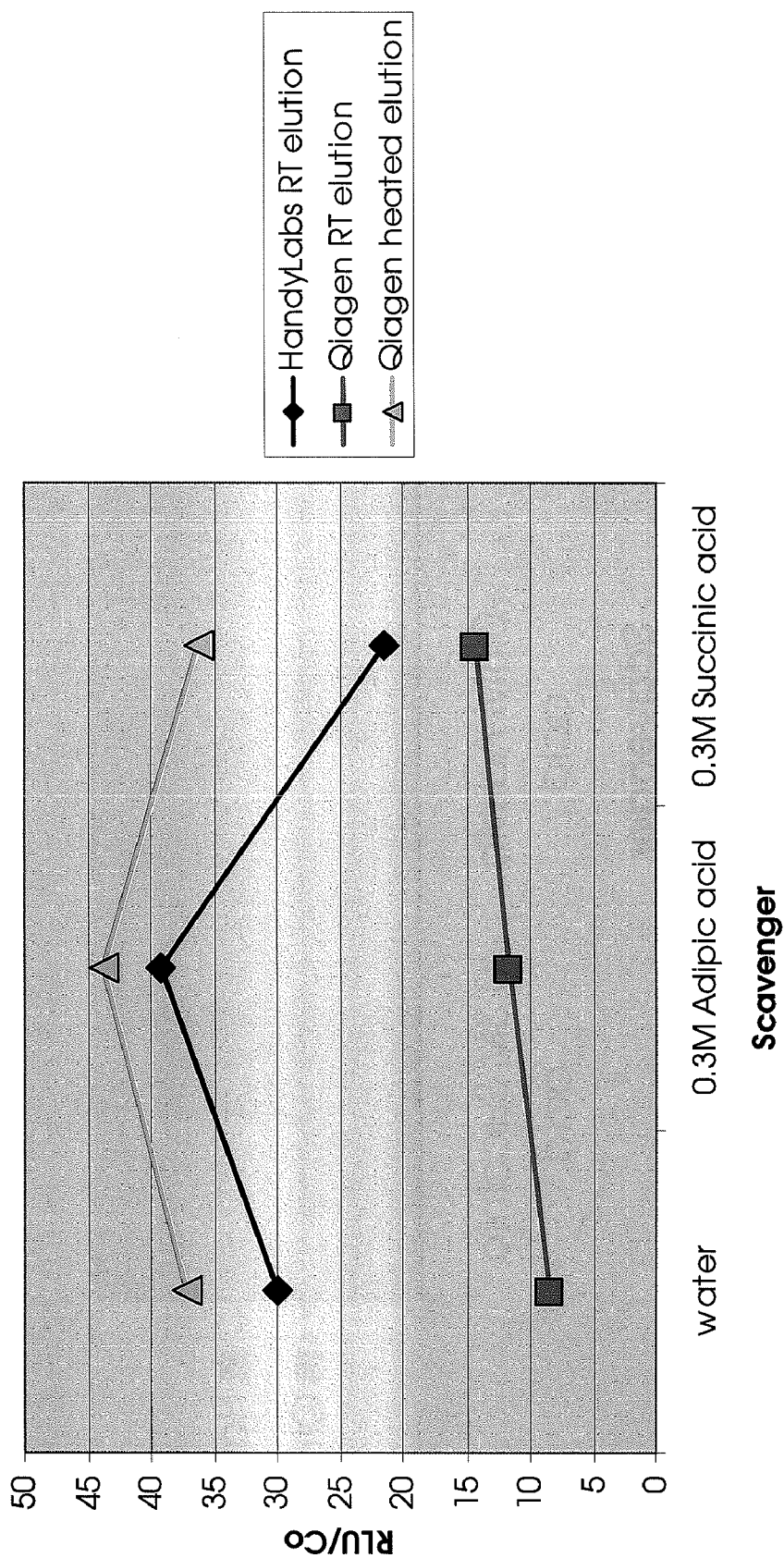
FIG. 9 demonstrates the performance of succinic acid dihydrazide and adipic acid dihydrazide in a QiaAmp extraction, where the elution step is performed at either room temperature (25° C.) or at 56° C.

It has been observed that the QiaAmp protocol is less compatible with SurePath medium than the HandyLabs protocol. It was therefore investigated whether increasing the temperature at which the nucleic acid is eluted from the anion exchange column could improve recovery. 20,000 SiHa cells were spiked into 500 µL of SurePath medium and processed according to either the HandyLabs protocol or the QiaAmp protocol set forth above using either 0.3M succinic acid dihydrazide or 0.3M adipic acid dihydrazide was the scavenger. For the QiaAmp protocol, elution was performed at either room temperature or 56° C. Results are shown at FIG. 9.

What is claimed is:

1. A method for extracting a target molecule from a biological sample preserved in a liquid cytology preservative solution, the method comprising:
   A) contacting the biological sample with a scavenger solution comprising a scavenging agent comprising at least one terminal hydrazine group;
   B) treating the biological sample under conditions sufficient to release the nucleic acid or protein from the biological sample; and
   C) isolating the target molecule,
wherein the scavenging agent is selected from the group consisting of:
   a) a compound according to formula I:

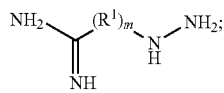

(I)

b) a compound according to formula II:

(II)

and
   c) semicarbazide; thiosemicarbazide; carbazide; thiocarbazide; N-aminoguanidine and a salt thereof; N,N-diaminoguanidine and a salt thereof; acetylhydrazide; adipic acid dihydrazide; succinic acid dihydrazide; formic hydrazide; maleic acid dihydrazide; malonic acid dihydrazide; benzenesulfonylhydrazide; tosylhydrazide; methylsulfonylhydrazide,
   wherein:
      $R^1$ $C_1$-$C_{12}$ alkyl; $C_1$-$C_{12}$ alkenyl; $C_3$-$C_6$ cycloalkyl; $C_3$-$C_6$ cycloalkenyl; $C_6$-$C_{10\ aryl;\ and\ C_6}$-$C_{10}$heteroaryl;
      $R^2$ which in each instance may be the same or different, and is selected from the group consisting of:

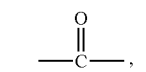

(i)

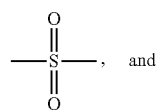

, and (ii)

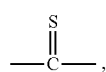

, (iii)

m is an integer selected from the group consisting of 0 and 1; and
n is an integer selected from the group consisting of 1 and 2;
wherein the scavenging agent is optionally modified so as to increase solubility in water.

2. The method of claim 1 wherein the scavenging agent is a compound of formula I wherein $R^1$ is $C_1$-$C_{12}$ alkyl and m is 1.

3. The method of claim 2 wherein $R^1$ is $C_1$-$C_6$ alkyl.

4. The method of claim 1 wherein $R^1$ is $C_2$-$C_4$ alkyl.

5. The method of claim 1 wherein the scavenging agent is a compound of formula II wherein $R^1$ is $C_1$-$C_{12}$ alkyl; $R^2$ is

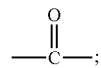

;

and n is 2.

6. The method of claim 5 wherein $R^1$ is $C_1$-$C_6$ alkyl.

7. The method of claim 5 wherein $R^1$ is $C_2$-$C_4$ alkyl.

8. The method of claim 1 wherein the scavenger solution comprises from about 0.1M to about 1.0M of the scavenging agent.

9. The method of claim 8 wherein the scavenger solution comprises from about 0.1M to about 0.5M of the scavenging agent.

10. The method of claim 8 wherein the scavenger solution comprises from about 0.2M to about 0.4M of the scavenging agent.

11. The method of claim 1 wherein the scavenger solution comprises about 0.3M adipic acid dihydrazide or about 0.3M succinic acid dihydrazide.

12. The method of claim 1 wherein the scavenger solution is added directly to the liquid cytology preservative solution.

13. The method of claim 1 wherein the scavenger solution further comprises a protein digestive enzyme.

14. The method of claim 1 wherein the biological sample is contacted with the scavenger solution before the target molecule is released from the biological sample.

15. The method of claim 1 wherein the target molecule is released from the biological sample by lysing the biological sample in the presence of a lysis solution.

16. The method of claim 15 wherein the scavenger solution is the lysis solution.

17. The method of claim 15 wherein the scavenger solution is added to biological sample before, after, or at the same time as the lysis solution is added to the biological sample.

18. The method of claim 1 wherein the target molecule is a target nucleic acid and:
   C) the target nucleic acid is isolated by a method comprising:
      (i) hybridizing a nucleic acid probe to the target nucleic acid with a second nucleic acid to form a nucleic acid hybrid;
      (ii) binding the nucleic acid hybrid to a solid phase;
      (iii) isolating the solid phase; and
      (iv) eluting the target nucleic acid from the solid phase.

19. The method of claim 18 wherein the nucleic acid hybrid is a DNA:RNA hybrid and wherein the DNA:RNA hybrid is bound to the solid phase by a method comprising contacting the nucleic acid hybrid with an antibody capable of binding to the nucleic acid hybrid, wherein the antibody is bound to the solid phase or adapted to be bound to the solid phase.

20. The method of claim 1 wherein the target molecule is a target nucleic acid and:
   C) the target nucleic acid is isolated by a method comprising:
      (i) binding the target nucleic acid to an anion exchange matrix; and
      (ii) eluting the target nucleic acid from the anion exchange matrix.

21. The method of claim 20 wherein the target nucleic acid is eluted from the anion exchange matrix at an elution temperature of from about 20° C. to about 70° C.

22. The method of claim 20, wherein the target nucleic acid is eluted from the anion exchange matrix at an elution temperature of from about 50° C. to about 60° C.

23. A lysis solution comprising:
(i) a buffer;
(ii) a detergent;
(iii) a scavenging agent comprising at least one terminal hydrazine group; and
(iv) optionally, protein digestive enzyme,
wherein the scavenging agent is selected from the group consisting of:
a) a compound according to formula I:

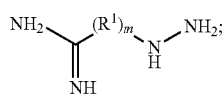
(I)

b) a compound according to formula II:

(II)

and c) semicarbazide; thiosemicarbazide; carbazide; thiocarbazide; N-amino guanidine and a salt thereof; N,N-diaminoguanidine and a salt thereof; acetylhydrazide; adipic acid dihydrazide; succinic acid dihydrazide; formic hydrazide; maleic acid dihydrazide; malonic acid dihydrazide; benzenesulfonylhydrazide; tosylhydrazide; methylsulfonylhydrazide, wherein:

$R^1$ is selected from the group consisting of: $C_1$-$C_{12}$alkyl; $C_1$-$C_{12}$alkenyl; $C_3$-$C_6$ cycloalkyl; $C_3$-$C_6$ cycloalkenyl; $C_6$-$C_{10}$ aryl; and $C_6$-$C_{10}$ heteroaryl, wherein $R^1$ is optionally substituted so as to increase the solubility of the scavenging agent in water;

$R^2$ which in each instance may be the same or different, and is selected from the group consisting of:

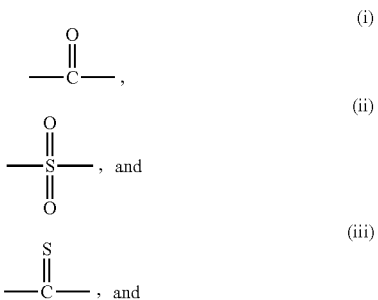

m is an integer selected from the group consisting of 0 and 1; and n is an integer selected from the group consisting of 1 and 2, wherein the scavenging agent is optionally modified so as to increase solubility in water.

24. The lysis solution of claim 23 comprising from about 0.1M to about 1.0M of the scavenging agent.

25. The lysis solution of claim 23 comprising from about 0.1M to about 0.5M adipic acid dihydrazide or from about 0.1M to about 0.5M succinic acid dihydrazide.

26. A kit for recovering a target nucleic acid from a biological sample preserved in a liquid cytology preservative solution, said kit comprising a lysis solution according to claim 23 and optionally comprising at least one additional component selected from the group consisting of: a protein digestive enzyme, a solid phase, a nucleic acid probe capable of hybridizing to the target nucleic acid, and an antibody.

* * * * *